(12) United States Patent
Wang et al.

(10) Patent No.: US 9,874,471 B2
(45) Date of Patent: Jan. 23, 2018

(54) LIQUID TRANSFER SYSTEMS AND METHODS OF CALIBRATION THEREOF BY PERFORMING AIR ASPIRATIONS

(71) Applicant: SIEMENS HEALTHCARE DIAGNOSTICS INC., Deerfield, IL (US)

(72) Inventors: Jianfang Wang, Wilmington, DE (US); Mark H. Sprenkle, Newark, DE (US); Jingjing Zhang, Newark, DE (US); John M. Shrewsbury, Elkton, MD (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 187 days.

(21) Appl. No.: 14/371,432

(22) PCT Filed: Jan. 9, 2013

(86) PCT No.: PCT/US2013/020867
§ 371 (c)(1),
(2) Date: Jul. 9, 2014

(87) PCT Pub. No.: WO2013/106457
PCT Pub. Date: Jul. 18, 2013

(65) Prior Publication Data
US 2014/0373596 A1    Dec. 25, 2014

Related U.S. Application Data

(60) Provisional application No. 61/585,326, filed on Jan. 11, 2012.

(51) Int. Cl.
*G01F 25/00*    (2006.01)
*G01N 35/10*    (2006.01)
(Continued)

(52) U.S. Cl.
CPC .......... *G01F 25/0092* (2013.01); *G01F 22/02* (2013.01); *G01L 27/002* (2013.01); *G01N 35/1016* (2013.01)

(58) Field of Classification Search
CPC ............... G01N 35/1016; B01L 3/0293; G01F 25/0092
(Continued)

(56) References Cited

U.S. PATENT DOCUMENTS 5,463,895 A * 11/1995 Brentz .................... G01F 23/14
                                                        73/61.71
5,750,881 A    5/1998  Dorenkott et al.
(Continued)

FOREIGN PATENT DOCUMENTS

EP    0810438 A2    12/1997
EP    2009449 A1    12/2008

OTHER PUBLICATIONS

PCT International Search Report and Written Opinion dated Mar. 12, 2013 (13 Pages).
(Continued)

*Primary Examiner* — Justin Olamit (57) ABSTRACT

Disclosed are methods adapted to calibrate a liquid transfer system. The methods include providing a probe having a fluidly-coupled pressure sensor, the pressure sensor adapted to sense an aspiration pressure associated with the probe, performing one or more air aspirations and taking one or more pressure readings with the pressure sensor, and using one or more of the pressure readings to calibrate the pressure sensor. A novel liquid transfer system is also disclosed, as are other aspects.

18 Claims, 5 Drawing Sheets

(51) Int. Cl.
  *G01F 22/02* (2006.01)
  *G01L 27/00* (2006.01)
(58) Field of Classification Search
  USPC .......................................................... 73/1.74
  See application file for complete search history.

(56) References Cited

U.S. PATENT DOCUMENTS

| | | | |
|---|---|---|---|
| 7,277,500 B2 * | 10/2007 | Saarnisaari | .......... H04B 1/7103 |
| | | | 375/316 |
| 7,396,512 B2 | 7/2008 | Ditrolio et al. | |
| 2004/0034479 A1 | 2/2004 | Shimase et al. | |
| 2008/0271514 A1 | 11/2008 | Viot et al. | |
| 2009/0075386 A1 | 3/2009 | Dunfee et al. | |
| 2009/0288470 A1 * | 11/2009 | Bentz | ...................... B01L 3/021 |
| | | | 73/1.74 |
| 2011/0111506 A1 | 5/2011 | Zuppiger | |

OTHER PUBLICATIONS

Extended EP Search Report dated Oct. 5, 2015 of corresponding European Patent Application No. 13736293.5, 3 Pages.

* cited by examiner

LIQUID TRANSFER SYSTEMS AND METHODS OF CALIBRATION THEREOF BY PERFORMING AIR ASPIRATIONS

RELATED APPLICATIONS

This application claims priority to U.S. Provisional Application Ser. No. 61/585,326 entitled "LIQUID TRANSFER SYSTEMS AND METHODS OF CALIBRATION THEREOF" filed on Jan. 11, 2012, the disclosure of which is hereby incorporated by reference in its entirety herein.

FIELD

The present invention relates generally to methods adapted to calibrate a liquid transfer system and systems adapted to carry out the calibration.

BACKGROUND

In medical testing and processing, the use of robotics may minimize exposure to, or contact with, bodily fluid samples (otherwise referred to as "specimens") and/or may significantly increase productivity. For example, in some automated testing and processing systems (e.g., clinical analyzers), a specimen and/or reagent liquid may be aspirated from one liquid-containing vessel and may be transferred to another liquid-containing vessel (e.g., a reaction cuvette, etc.).

Such liquid transfer may be accomplished by the use of a robotic mechanism, which may include a suitable moveable robotic component and an attached probe. The probe may be moved in one or more coordinate directions by the robotic component. In this manner, the probe may aspirate a specimen or reagent liquid from a first liquid-containing vessel, and then move and dispense the specimen or reagent liquid into another liquid-containing vessel.

During the aspiration step, it is desirable to check/verify whether a correct volume of the specimen or reagent liquid has indeed been aspirated. Accordingly, conventional systems may include a pressure sensor that is used to monitor a representative aspiration pressure as the specimen or reagent liquid is being aspirated. Furthermore, such conventional systems may undergo a calibration step to calibrate the pressure sensor by aspirating a liquid (e.g., a reagent liquid) in order to establish a baseline reference value against which other pressure readings taken during the testing will be compared.

Notably, however, inaccuracies in the calibration may result in inaccurate judgment being made about whether, for example, a sufficient amount of the specimen or reagent liquid has in fact been aspirated. Thus, accurate calibration may be important to improve accuracy of testing results. When the size (e.g., volume) of the specimen or liquid reagent being aspirated is relatively small, proper calibration becomes especially important.

Accordingly, methods and systems that may improve an accuracy or reliability of liquid aspiration are desired.

SUMMARY

In a first method aspect, a method of calibrating a liquid transfer system is provided. The method includes providing a probe having a pressure sensor fluidly coupled to the probe, performing one or more air aspirations and taking one or more representative pressure readings with the pressure sensor, and using one or more of the representative pressure readings to carry out calibration of the pressure sensor.

According to another aspect, a method of calibrating a liquid transfer system is provided. The method includes providing a probe having a pressure sensor fluidly coupled to the probe, the pressure sensor adapted to sense a representative aspiration pressure, moving the probe to a defined location in space above a liquid-containing vessel, performing multiple air aspirations at the defined location wherein at least some of the multiple air aspirations are at a different aspiration flow rate and at least some of the multiple air aspirations are at a different aspiration volume, recording pressure readings of at least some of the multiple air aspirations, and using at least some of the recorded pressure readings to determine a representative pressure reference value for the pressure sensor.

In a system aspect, a liquid transfer system is provided. The liquid transfer system includes a probe, a pressure sensor fluidly coupled to the probe, the pressure sensor adapted to sense a representative aspiration pressure, and a controller configured and operational to perform one or more air aspirations and record at least one pressure reading based upon the one or more air aspirations, and determine a representative pressure reference value for the pressure sensor based on the at least one pressure reading.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. Moreover, like reference numerals are used herein to denote like elements. The invention is to cover all modifications, equivalents, and alternatives falling within the scope of the invention.

DETAILED DESCRIPTION

In automated liquid transfer systems utilized, for example, in clinical analyzers, achieving a determination of proper liquid volume aspiration by one or more probes contained in the liquid transfer system is desirable. In current liquid transfer systems used in clinical analyzers, smaller and smaller liquid volumes are being aspirated. Accordingly, not only do very small amounts of specimen need to be accurately aspirated and delivered (e.g., dispensed), even smaller amounts of reagent liquid need to be precisely aspirated and dispensed. In some instances, small volumes of other liquids may also need to be accurately aspirated and dispensed. Accordingly, very precise calibration is desired so that accurate judgments may be made about whether a sufficient volume of specimen, reagent liquid, or other liquid have been properly aspirated by the liquid transfer system.

As discussed above, in such liquid transfer systems, the liquid aspiration may be carried out by a probe while monitoring a representative aspiration pressure within the liquid transfer system. In particular, a representative aspiration pressure during liquid aspiration is monitored by monitoring pressure readings from a pressure sensor that is fluidly coupled to the probe. In some liquid transfer systems, more than one probe may be provided, with a pressure sensor being associated with each probe.

Figure 2A:
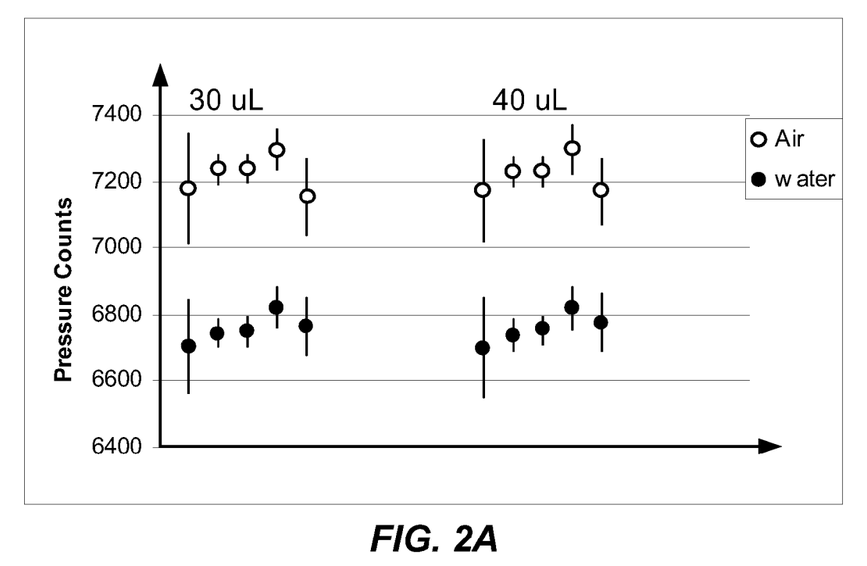
FIG. 2A is a graphical plot illustrating pressure variations between probes aspirating both air and water in a liquid transfer system having multiple probes according to embodiments.
Figure 2B:
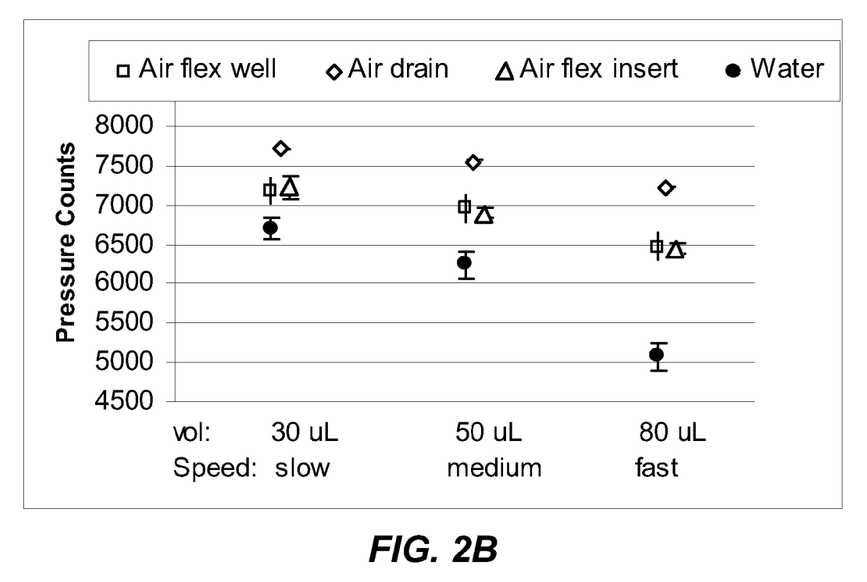
FIG. 2B is a graphical plot illustrating pressure variations for a probe aspirating both air and water taken at different locations, aspiration volumes, and aspiration flow rates in a liquid transfer system according to embodiments.
Figure 2C:
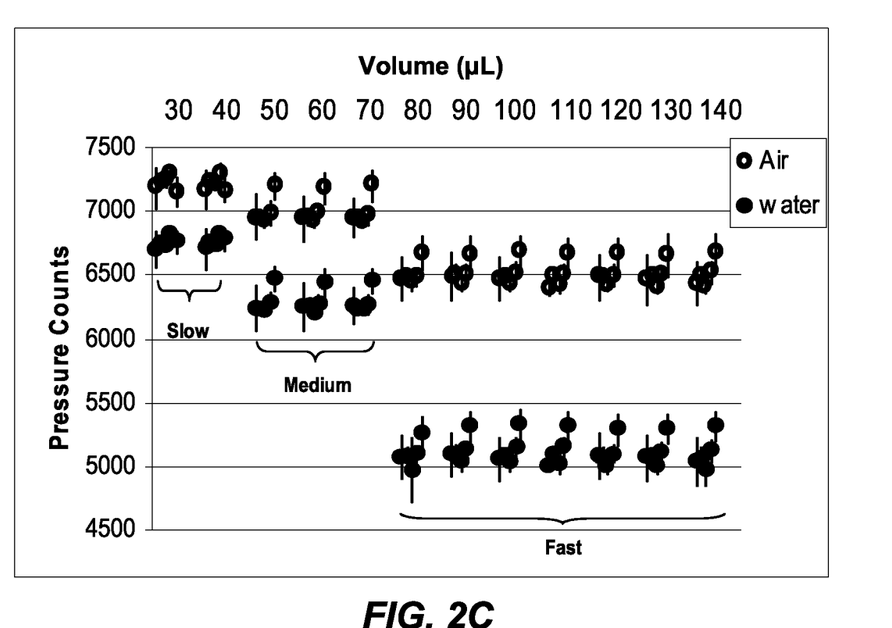
FIG. 2C is a graphical plot illustrating pressure variations aspirating both air and water at different aspiration volumes and flow rates in a liquid transfer system according to embodiments.
Figure 2D:
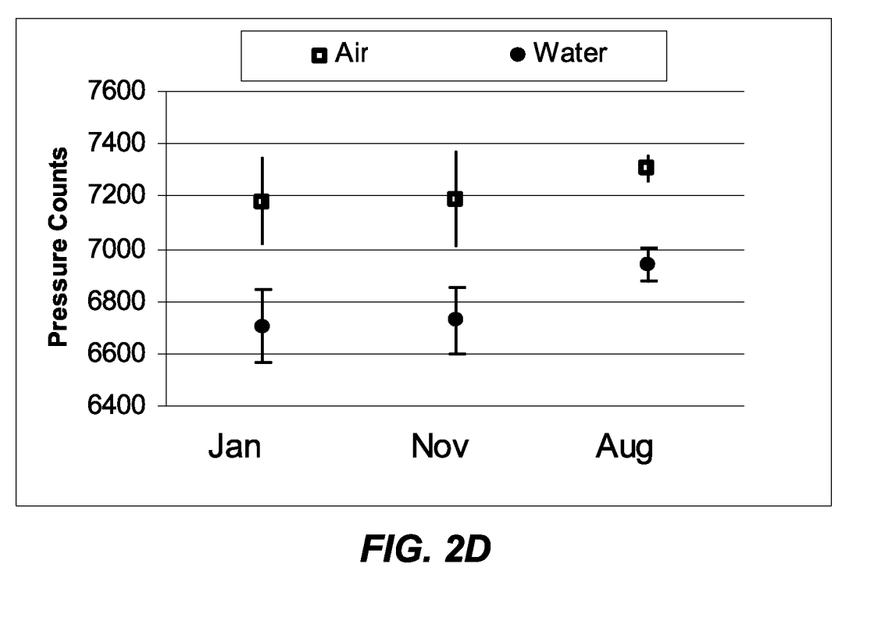
FIG. 2D is a graphical plot illustrating pressure variations over time while aspirating both air and water in a liquid transfer system according to embodiments.

Investigations by the inventors herein have determined that pressure readings may vary per probe in clinical analyzers having multiple probes (see FIG. 2A), demonstrating variations from probe-to-probe in a five-probe system. Furthermore, it was also discovered that the pressure readings may vary based upon a location of the probe in space when the pressure reading is taken (see FIG. 2B). Moreover, FIGS. 2B and 2C also illustrate variations in pressure readings when taken at slow, medium, and fast aspiration flow rates. Additionally, it was noted that pressure variations may also occur over time (see FIG. 2D) due to changes in ambient temperature and/or pressure, as well as due to drift in the processing electronics and pressure sensor. Most importantly, however, through their investigation the inventors have discovered that aspirating air through the probe may be approximately correlated to pressures experienced when aspirating a liquid. Water was used in the experimental testing, but reagent liquids and other bodily fluid show similar correlations. Accordingly, methods that are adapted to improve accuracy, reliability, and/or efficiency of calibration of pressure sensors in liquid transfer systems including probes are desired.

In view of the foregoing problems, embodiments of the present invention provide, in one aspect, improved calibration methods adapted to calibrate liquid transfer systems containing one or more probes. In a first aspect, the method includes aspirating air, rather than reagent liquid used in prior art systems for carrying out pressure sensor calibration. In this manner, not only is reagent liquid saved, but relatively quick calibration may be carried out. Thus, calibration may be carried out more frequently. The method includes performing one or more air aspirations and taking one or more pressure readings with a pressure sensor, followed by using one or more of the pressure readings to carry out a calibration of the pressure sensor.

In another aspect, a liquid transfer system is provided that is adapted to carry out calibration of the pressure sensor using one or more air aspirations (e.g., multiple air aspirations). According to another aspect of the invention, each probe should be separately calibrated because of the above-noted probe-to-probe variations.

These and other aspects and features of the invention will be described with reference to FIGS. 1-4 herein.

Figure 1:
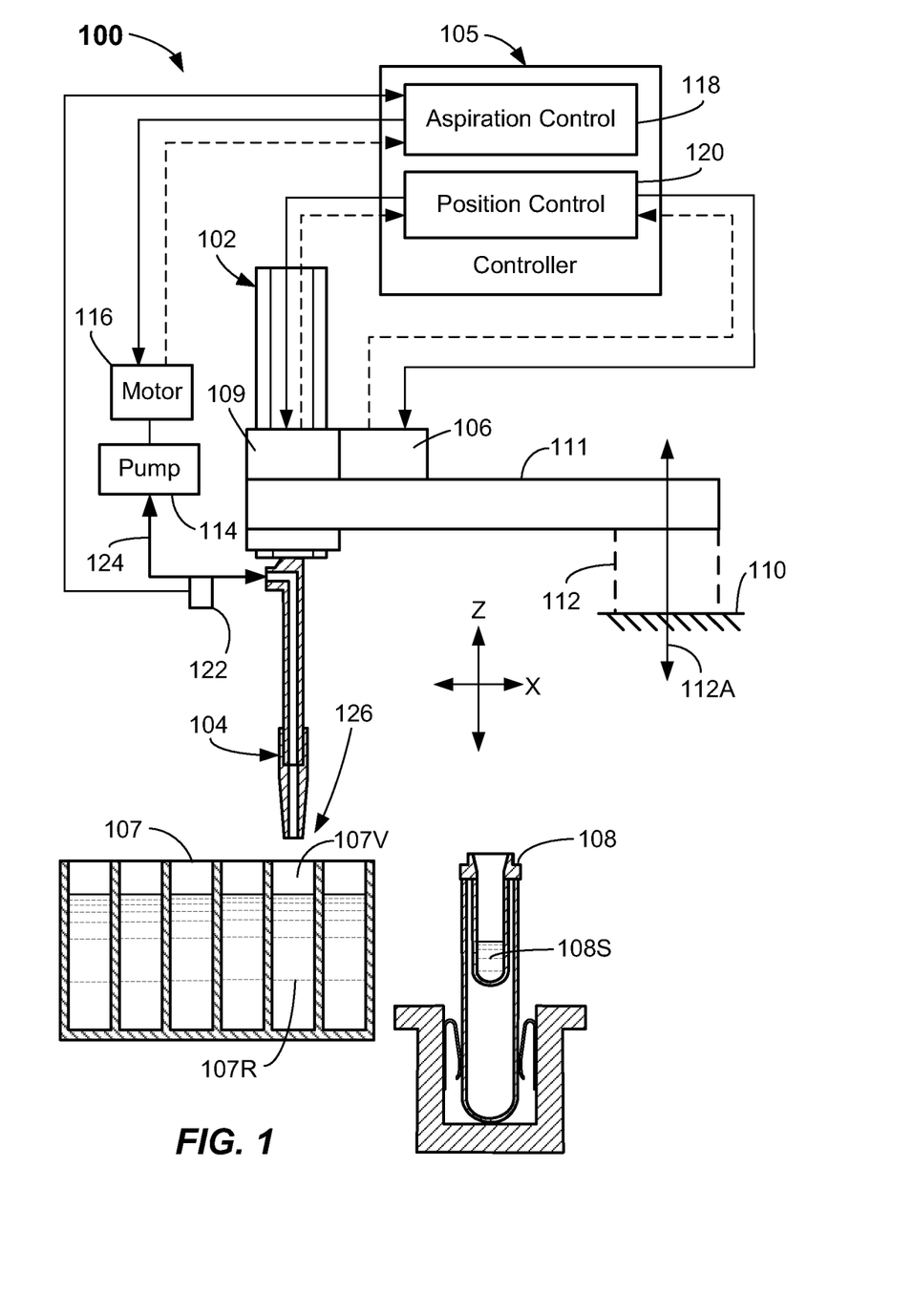
FIG. 1 is a partially cross-sectioned side view illustration of a liquid transfer system according to embodiments.

In accordance with a first embodiment of the invention, as best shown in FIG. 1, a liquid transfer system 100 is described. The liquid transfer system 100 is configured and operational to carry out a calibration method according to another aspect. The liquid transfer system 100, in some embodiments, is included in an automated clinical analyzer, or other processing or testing system (e.g., a biological fluid specimen processing or testing system). In particular, the liquid transfer system 100 is useful for precisely transferring a desired volume of a liquid. The liquid may be transferred from one location to another. For example, the liquid transfer system 100 may be used to aspirate a precise volume of a biological liquid (e.g., blood, blood plasma, blood serum, interstitial fluid, urine, spinal fluids, or the like) and then dispense that liquid at another location or into another vessel. Similarly, the liquid transfer system 100 may be used to aspirate and dispense a precise volume of a reagent liquid. Such reagent liquid may be aspirated from a reagent-containing vessel (e.g., a Flex® reagent cartridge) and dispensed into another vessel. In some instances, the liquid may be transferred from one location to another location by the liquid transfer system 100. The liquid transfer system 100 may be useful for transferring relatively small volumes of the liquid, such as between about 10 µL to about 150 µL. However, other liquid volumes may be transferred as well.

The liquid transfer system 100 includes a robotic component 102 having a probe 104 coupled thereto. The probe 104 may be either directly connected to or interconnected to the robotic component 102. The probe 104 is moveable in space by the robotic component 102. The liquid transfer system 100 may include a suitable controller 105 that may command the robotic component 102 and attached probe 104 to move in space. For example, the robotic component 102 may move the probe 104 to one or more defined locations in space. In particular, the controller 105 may command the robotic component 102 to move in one or more coordinate directions (e.g., in an X, Y, or Z direction), two or more coordinate directions (e.g., X and Z, Y and Z), three or more coordinate directions (e.g., X, Y, and Z, or X, R, and Z), where X is side-to-side motion, Y is motion into and out of the paper in FIG. 1, R is rotational motion about an axis (e.g., axis 112A), and Z is vertical motion. The controller 105 may be any suitable electronic controller adapted to interact with the robotic component 102, and may include a suitable microprocessor, memory, power supply, conditioning electronics, one or more feedback sensors, and electronic circuitry adapted to carry out the one or more coordinate motions of the probe 104.

In the depicted embodiment, an X-Z robot is shown. However, it should be recognized that any suitable robotic component 102 may be used. For example, a moveable multi-arm robot having one or more shoulder, elbow, or wrist elements may be used. Optionally, a telescopic boom robot may be used, where the probe 104 is coupled to the boom. In other embodiments, a robotic component having one or more beams having one or more coupled motors may be used, wherein the probe 104 is coupled to one of the beams or to a gantry arm. Thus, any suitable mechanism for imparting motion to the probe 104 may be used.

In one implementation, the robotic component 102 may be used to accomplish at least two-dimensional coordinate motion (e.g., X and Z) of the probe 104. In this manner, for example, the probe 104 may be moved in the X direction to a location above a first liquid-containing vessel 107V (e.g., a single vessel of a reagent-containing container 107 including multiple vessels the same or similar to first liquid-containing vessel 107V). The probe 104 may be lowered in the Z direction into the liquid (e.g., reagent liquid 107R) contained in the first liquid-containing vessel 107V, and may aspirate a precise volume of reagent liquid 107R into the probe 104. Additionally, the robotic component 102 may accomplish an upward retraction motion of the probe 104 in the Z direction and then motion in the X direction to a location above a second vessel 108 (e.g., a sample container) wherein the reagent liquid 107R may be dispensed. The dispensing may typically involve lowering the probe 104 in the Z direction to a point in or just above the second vessel 108 where the liquid reagent 107R is dispensed. Similarly, aspiration and dispensing of a specimen 108S may occur, wherein the specimen 108S and reagent liquid 107R may be mixed in the second vessel 108. A reaction between the specimen 108S and the reagent fluid 107R may then be carried out. Other fluid may also be included, such as purified water.

The robotic component 102 may include one or more motion-producing components integral therewith or coupled thereto. For example, an X-axis motor 106 may be provided that is configured and operational to impart X-axis motion to the probe 104 relative to a frame 110 of the testing or processing system. For example, the X-axis motor 106 may be coupled to a Z-axis motor 109 adapted to move the robotic component 102, either directly or through a bracket, such that the X-axis motor 106 moves the robotic component 102 along a length of a guide beam 111. The Z-axis motor 109 may be configured and operational to cause Z-axis motion of the probe 104 relative to the beam 111 and frame 110. In some embodiments, another motor 112 may impart a Y-axis motion of the robotic component 102 relative to the frame 110. In this configuration, X, Y, and Z motion of the probe 104 may be carried out to accomplish complex fluid transfer motion profiles. Optionally, motor 112 may be a rotational motor imparting rotation of the beam 111 about an axis 112A. Suitable feedback mechanisms may be provided for each degree of motion, such as by using position and/or rotation sensors. In the absence of the motor 112, the beam 111 may be directly attached to the frame 110 or otherwise rigidly connected to the frame 110 through an intermediate member.

In the depicted embodiment, the robotic component 102 may include suitable tracks or guides to restrict motion to a vertical motion along the Z axis. Furthermore, drive systems including sprocket and chain, pulley and belt, rack and pinion, gear or worm drives or other conventional drive components may be utilized to cause the various motions of the robotic component 102. Other types of robotic components 102 may be employed. The motors 106, 109, 112 may be any suitable motor type, such as one or more stepper motors, servo motors, pneumatic or hydraulic motors, electric motors, linear motors, or combinations thereof.

Again referring to FIG. 1, the liquid transfer system 100 includes a pump 114. The pump 114 may be connected to the probe 104 and driven to aspirate and/or dispense accurate volumes of liquids (e.g., liquid reagent and/or biological fluid specimen). The pump 114 may be driven by a suitable pump motor 116, such as a stepper motor, for example. Other suitable motors may be used. The pump 114 may be any type of pump suitable for dispensing relatively small liquid volumes, such as a piston pump.

The pump 114 is driven in response to control signals from the aspiration control module 118 of the controller 105. Aspiration control module 118 may be a separate part of the controller 105 or integrated with the position control module 120. For example, each module 118, 120 may include suitable control signal conditioning components such as filters, analog-to-digital converters, and/or amplifiers to send signals to the respective pump motor 116 and robot motors 106, 109, and 112 and receive feedback signals therefrom. Controller 105 may include a common microprocessor and memory for carrying out pre-programmed position and aspiration control instructions. Optionally, separate intercommunicating microprocessors and memories may be used to carry out position control and aspiration control.

The liquid transfer system 100 includes a pressure sensor 122 fluidly coupled to the probe 104. For example, the pressure sensor 122 may be configured and functional and thus adapted to sense a representative aspiration pressure associated with the probe 104. The aspiration control module 118 may receive electronic signals (e.g., voltage signals) from a pressure sensor 122. The pressure sensor 122 is configured and operational and thus adapted to measure and supply pressure readings associated with the aspiration by the probe 104. For example, the pressure sensor 122 may be coupled to the probe 104 or, as shown, coupled to a conduit 124 fluidly connecting the pump 114 and the probe 104.

As previously mentioned, the liquid transfer system 100 is adapted to transfer liquid, such as from one vessel to another or one location to another. As part of this transfer, in a method aspect, a calibration may be carried out. The calibration is carried out in order to establish a representative pressure reference value for each probe 104 in the fluid transfer system 100. In particular, the calibration method may be carried out before each liquid aspiration, before every few liquid aspirations, before a lot of liquid aspirations (e.g., a lot of tests), only at start-up of the clinical analyzer including the liquid transfer system 100, etc. Other frequencies of calibration may be used. However, it should be recognized that because the representative pressure reference value is established via aspirating air, no reagent material needs to be aspirated and/or discarded as part of the calibration method. Moreover, calibration may be quickly and efficiently carried out. Accordingly, a higher number of calibrations may be carried out in order to verify system operation, with little overall associated cost. Moreover, because the calibration may be carried out more frequently, the aforementioned effect of drift may be minimized.

The method of calibrating a liquid transfer system 100 will now be described in detail with reference to FIG. 1. In the depicted embodiment, the calibration method for a first probe 104 is carried out. Individual calibrations, the same as will be described herein, may be carried out for each other probe 104 in the liquid transfer system 100 (only one probe 104 shown). As a first part of the method, the probe 104 may be moved to a defined location in space prior to performing one or more air aspirations. In particular, the probe 104 may be positioned at a first location 126. The first location 126 is preferably located in very close proximity to the liquid-containing vessel 107V. For example, the defined location in space may be over the liquid-containing vessel 107V. For example, if the liquid being aspirated is a reagent liquid 107R, then the liquid-containing vessel 107V is a reagent container 107, and the probe 104 is positioned over the liquid-containing vessel 107V. The defined location in space may be located less than about 20 mm from a top of the liquid-containing vessel 107V. For example, the probe 104 may be placed at about 2 mm from the top of the liquid-containing vessel 107V. Positioning the probe 104 very close to the liquid-containing vessel 107V to carry out the calibration minimizes pressure variations due to the location of the probe 104 in space.

Once positioned at the defined first location 126, the aspiration control module 118 initiates a signal to the pump motor 116 to actuate (e.g., reciprocate) the pump 114 and one or more air aspirations are undertaken by aspirating air into the probe 104 and then expelling the air. One or more pressure readings are taken with the pressure sensor 122. For example, the pressure sensor 122 may provide an output of a varying voltage signal to the aspiration control module 118. The varying voltage signal is then processed to extract peak values associated with peak pressures for each of the multiple air aspirations. Any suitable peak-finding algorithm may be used to find the peak value (e.g., value of the peak voltage that is correlated to peak pressure), such as a sample-and-hold algorithm. A sample-and-hold algorithm samples the pressure readings at certain time increments and compares the sampled value to a previously-held value to determine the peak value for each aspiration cycle. Optionally, the peak value may be determined by extracting one or more values at a defined time in the aspiration cycle.

The air aspirations of the calibration method may be carried out at any suitable frequency, such as between about and 120 aspirations per minute. Other aspiration frequencies may be used. For example, in one implementation, multiple air aspirations are carried out at the first location in space 126 without moving the probe 104. The multiple air aspirations may be carried out at more than one air aspiration flow rate and/or at more than one air aspiration volume. At least some of the one or more pressure readings for at least some of the one or more air aspirations are recorded. For example, each one of the pressure peak readings may be stored in memory of the controller 105 associated with the aspiration control module 118.

In the depicted embodiment, once the one or more peak pressure readings are obtained, a representative pressure reading may be determined and used for calibration of the pressure sensor 122. The representative pressure reading may then be used as a representative pressure reference value for the liquid transfer system 100 when transferring liquid. In one example, the representative pressure reference value may be an arithmetic average of multiple sequential pressure peak readings that are taken. Optionally, in another example, the representative pressure reference value may be a median value of the multiple peak pressure readings that have been taken.

As shown in Table 1 below, in some embodiments, the multiple air aspirations may include three or more air aspirations at a single condition, i.e., at a preset flow rate and/or preset flow volume. In other embodiments, the multiple air aspirations may include five or more air aspirations at a single condition. As shown in Table 1, in some embodiments, at least two of the multiple air aspirations are carried out by aspirating air at different air volumes. For example, given that the liquid transfer system 100 may be used for multiple tests, some at very low volumes and some at relatively higher volumes, a representative pressure sampling may be taken for one or more of the known or expected sampling conditions.

In some embodiments, if the expected or known testing is to be carried out at a liquid aspiration volume of between 0-29.0 µL, then five pressure peak readings may be taken at an air aspiration volume of about 29 µL. Likewise, if the expected or known testing is to be carried out at a higher volume, a representative pressure reference value may also be determined at a higher volume. For example, if the testing is to be carried out at a liquid aspiration volume of between 29.1-46.4 µL, then five pressure readings may be taken at an air aspiration volume of about 46 µL. The five pressure readings may be taken at an air aspiration flow rate of about 150 µL/sec. Additional readings may be taken for other known or expected liquid volume aspiration ranges.

Additionally or optionally, the one or more air aspirations may be carried out at more than one air aspiration flow rate. For example, if the expected or known testing is to be carried out at a liquid aspiration volume of between 0-29.0 µL, then five pressure readings may be taken at an air aspiration flow rate of about 150 µL/sec. Likewise, if the testing is to be carried out at a liquid aspiration volume of between 29.1-46.4 µL, then five pressure readings may be taken at a relatively higher air aspiration flow rate of about 250 µL/sec. Additional readings at different flow rates may be taken for any other liquid volume aspiration range(s). Thus, in some embodiments, at least two or more of the multiple air aspirations are carried out by aspirating at different air aspiration flow rates.

Figure 3:
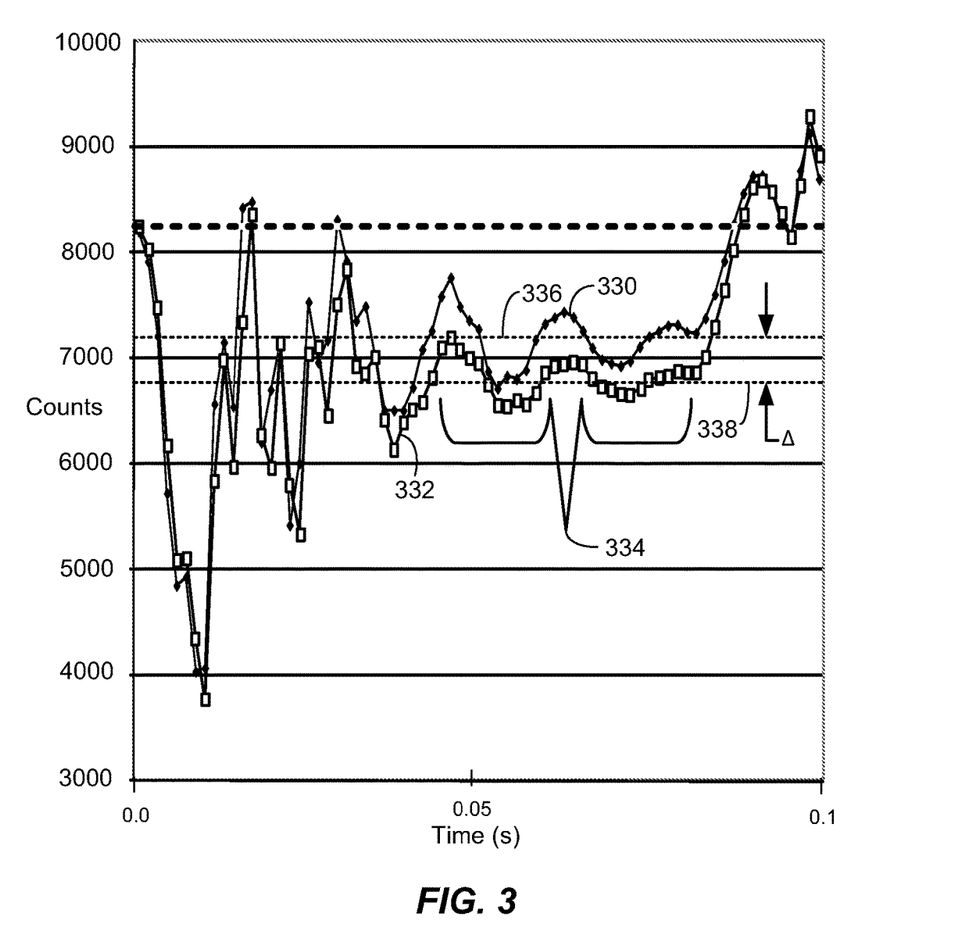
FIG. 3 is a graphical plot illustrating air and liquid traces over time while aspirating both air and water in a liquid transfer system according to embodiments.

In some embodiments, an entire panel of pressure readings may be taken as part of the calibration method. The panel may be taken at a number of different air aspiration flow volumes and/or a number of different air aspiration flow rates and representative pressure readings recorded. From these recorded representative pressure readings (e.g., voltage values or counts correlated with measured pressures), a number of representative pressure reference values may be determined. For example, five representative pressure readings may be taken at each air aspiration flow volume and each air aspiration flow rate, the values recorded, and a representative pressure reference value determined for each condition. The actual readings for each aspiration may be distilled or averaged from multiple samplings taken for each air aspiration. For example, 20+ sample readings may be taken for each air aspiration and then averaged, thus providing a representative pressure reading for each respective aspiration. For example, as shown in FIG. 3, a liquid aspiration trace 332 and an air aspiration trace 330 are shown. The traces 330, 332 represent instantaneous pressure readings taken over time during aspirations of air and water, respectively. The sampling of readings from the air aspiration trace 330 is taken during the calibration method from a settled region 334 of the air aspiration trace 330. The settled region 334 may be selected based upon experiments determining a settling time for transients of the pump motor 116 at each aspiration flow rate. A representative pressure reading is determined for each respective air aspiration based upon averaging the sample readings (e.g., 20+ readings) taken over the settled region 334. A representative pressure reference value 336 may be determined by sorting each of the representative pressure readings obtained for aspiration at each condition. The representative pressure reference value 336 may be obtained, for example, by selecting the median of the representative pressure readings as the representative pressure reference value at that particular condition. Notably, in the depicted embodiment, the representative pressure reference value 336 is actually a voltage count.

Accordingly, these representative pressure reference values (e.g., 336) obtained at each condition may be stored in memory of the controller 105 and may be used in the liquid transfer system 100 to calibrate, i.e., verify, that an appropriate amount of liquid has indeed been aspirated during an aspiration.

Thus, in a first aspect, it should be apparent that at least two of the multiple air aspirations may be carried out by aspirating at different aspiration flow rates. In another aspect, it should be apparent that at least two of the multiple air aspirations may be carried out by aspirating at both different air aspiration volumes and at different aspiration flow rates. Additionally, the calibration may be carried out by using a first set of air aspirations at a first aspiration flow rate, and a second set of aspirations at a second aspiration flow rate wherein the second air aspiration flow rate is different from the first aspiration flow rate. Furthermore, in some embodiments, the calibration may be carried out by using a first set of air aspirations at a first aspiration flow rate and at a first aspiration volume, and a second set of aspirations at a second aspiration flow rate and a second aspiration volume, the second air aspiration flow rate being different from the first aspiration flow rate, and the second air aspiration volume being different from the first aspiration volume. Other numbers of sets of air aspirations may be carried out across an expected liquid aspiration range for the liquid transfer system 100.

TABLE 1

Probe Aspiration Volumes and Flow Rates

| Aspiration pump speed | Aspiration flow rate (uL/Sec) | Liquid Aspiration volume range (uL) | Aspiration Air volume (uL) |
|---|---|---|---|
| Super Slow | 150 | 0-29.0 | 29 |
| Slow | 250 | 29.1-46.4 | 46 |
| Medium | 330 | 46.5-72.8 | 72 |
| Fast | 500 | 72.9-150 | 75 |

Thus, the one or more representative pressure reference values (e.g., 336) obtained from the air aspirations carried out during the calibration method may be used by the liquid transfer system 100 when aspirating a volume of a specimen or a reagent liquid. The representative pressure reference value (e.g., 336) obtained from the calibration of the pressure sensor 122 is used to determine if a sufficient volume of the specimen or the reagent liquid has in fact been aspirated. Of course, in a liquid transfer system 100 having multiple probes, separate calibrations via one or more air aspirations may be carried out for each probe. Thus, one or more representative pressure reference values may be determined for each probe. For example, a number of representative pressure reference values may be determined at a number of different volume and/or flow rate conditions for each probe. These are stored in memory and used later to verify subsequent liquid aspirations.

Given that each representative pressure reference value is nicely correlated with the pressure readings of the pressure sensor 122 when aspirating a liquid at that condition, a pressure delta value (Δ) can be established and used by the aspiration control module 118. As shown in FIG. 3, a representative liquid pressure value 338 may be determined experimentally, such as in an initial system setup step, by aspirating an amount of liquid (e.g., water) at a same or similar flow rate condition as the air aspirations will be taken and generally over the same settled region 334. A representative pressure reading may then be determined by averaging multiple (20+) liquid aspiration readings over the settled region 334. This may be repeated multiple times. The representative pressure reference value 338 for the liquid aspiration may be stored in the memory of the aspiration control module 118. This stored representative pressure reference value 338 may be subsequently used during aspiration of a reagent liquid or other biological fluid by the liquid transfer system 100.

During the calibration method, a pressure delta value (Δ) is determined. The pressure delta value (Δ) is based upon a difference between the representative pressure reference value 338 for the liquid aspiration and a representative pressure reference value 336 for the one or more air aspirations carried out during the calibration. For example, if the air aspirations are repeated multiple times at a condition, then the representative pressure reference value 336 for the air aspiration may be a median value of the multiple readings. The pressure delta value (Δ) (e.g., which may be a unit-less voltage count delta) may then be stored in memory. Based on this saved pressure delta value (Δ) determined during calibration, proper liquid aspiration during later use of the liquid transfer system 100 may be determined.

In one example, aspiration resulting in less than a predetermined percentage of the pressure delta value (Δ) during aspiration of a liquid during liquid transfer can be indicative of a defective aspiration. For example, if a representative pressure reading from the pressure sensor 122 is too high, then the aspiration may be deemed improper. A value below the predetermined percentage (e.g., 25% -75%) of the pressure delta value (Δ) generally indicates that insufficient liquid has been aspirated. Likewise, a value above the predetermined percentage (e.g., 25% -75%) of the pressure delta value (Δ) generally indicates that sufficient liquid has been aspirated. The predetermined percentage of the pressure delta value (Δ) may be set based upon experience, for example.

To aid in achieving a better understanding of the calibration method, the following mathematical relationships are provided. The calibration method creates a representative pressure reference value in order to minimize or eliminate a ΔP(System) effect. The ΔP(System) effect is a collective sum of system pressure variations due to many variables, e.g., changes from time-to-time, changes in ambient temperature and/or pressure, or aspiration locations, etc. According to the calibration method, air is aspirated at a predefined volume V, based on a specific pump speed (resulting in a specific flow rate) and an air pressure reading ($P_{Air}$) is measured and recorded.

$$P_{Air}=P_{Air}(\text{System})+P_{Air}(V)$$

$P_{Air}(V)$ is part of $P_{Air}$ due to aspiration of air of the predefined volume V. The probe 104 may take multiple air aspirations at the defined first location 126 proximate to the liquid-containing vessel 107V (calibrating the probe and location factors). In one example, it takes only about ten seconds to create the representative pressure reference value(s). Accordingly, collection of the representative pressure reference value(s) may be taken frequently (e.g., many times a day) and used for calibration updates.

When a liquid aspiration is carried out, then the liquid pressure ($P_{Liq}$) is measured and recorded. where $$P_{Liq}=P_{Liq}(\text{System})+P_{Liq}(V)$$

The liquid aspiration is carried out under generally the same conditions as the air reference pressure generations. Accordingly, then:

$$P_{Air}(\text{System}) \approx P_{Liq}(\text{System})$$

and $$P_{Air}-P_{Liq}=P_{Air}(V)-P_{Liq}(V)=\Delta$$

Thus, $P_{Air}$ or $P_{Liq}$ is the total instrument reported pressure when the probe 104 aspirates either air or liquid of volume V, which all include the P(System) effects. $P_{Air}(V)-P_{Liq}(V)$ then becomes a measure of whether of the pressure delta value (Δ), which may be used to determine if the fluid aspiration is short of the intended aspiration volume. Therefore, a delta of $P_{Air}-P_{Liq}$=pressure delta value (Δ) may be used as a direct measure of whether the fluid aspiration is short with minimum impact of P(System) pressure variations.

Figure 4:
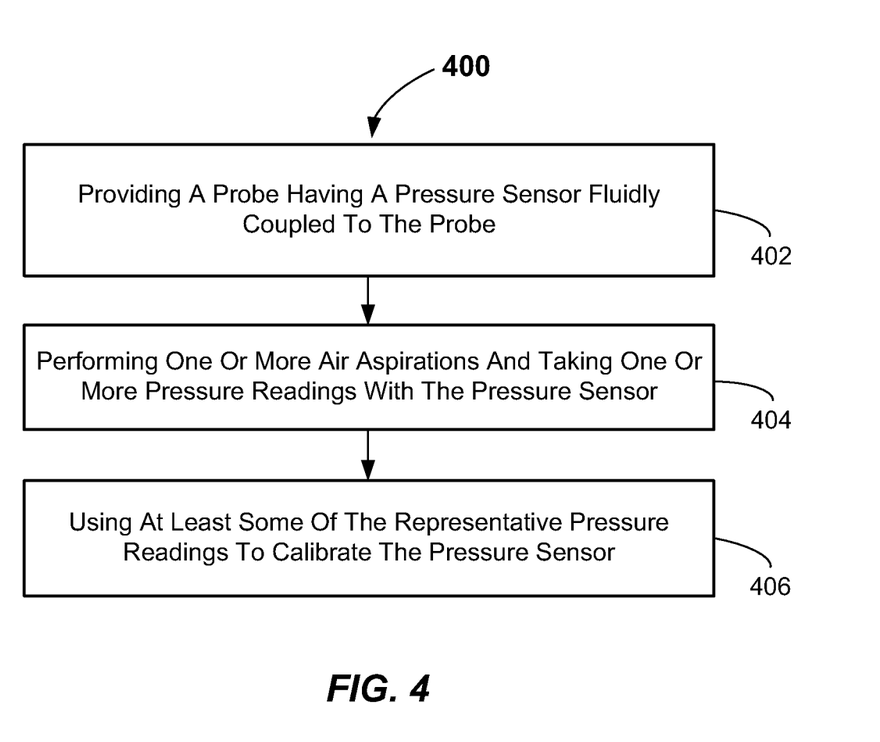
FIG. 4 is a flowchart illustrating a method of calibrating a liquid transfer system according to embodiments.

The method 400 of calibrating a liquid transfer system (e.g., liquid transfer system 100) according to embodiments of the invention will now be explained in detail with reference to the flowchart shown in FIG. 4 and the liquid transfer system 100 shown in FIG. 1. The method 400 includes, in block 402, providing a probe (e.g., probe 104) having a pressure sensor (e.g., pressure sensor 122) fluidly coupled to the probe. The pressure sensor may be adapted to sense an aspiration pressure associated with the probe. In block 404 of the method 400, performing one or more air aspirations and taking one or more pressure readings with the pressure sensor is carried out. In one implementation, the one or more air aspirations may include multiple air aspirations for each probe in the liquid transfer system. The multiple air aspirations may be accomplished at different air flow rates and/or different air flow volumes, or both. In block 406 of the method 400, using the one or more of the pressure readings to carry out calibration of the pressure sensor is accomplished. The one or more pressure readings are used to determine a representative pressure reference value for each probe. The one or more representative pressure reference values may be stored in memory and used to verify that a sufficient amount of a liquid is actually aspirated during a later liquid aspiration step in operation of the liquid transfer system 100.

In operation of the liquid transfer system 100, the measured liquid pressure value may be subtracted from the representative pressure reference value, and a determination made of whether the liquid aspiration is short in volume. For example, if the pressure delta value ($\Delta$) is less than a preset fraction or percentage of the pressure delta value ($\Delta$), then this may indicate a failure of the pump 114, conduit 124, probe 104, or robotic component 102, or an insufficient amount of reagent liquid 107R remaining in the liquid-containing vessel 107V. Accordingly, the liquid transfer system 100 may be stopped or a warning issued to the operator thereof. By utilizing the present calibration method 400, confidence in test results is improved because knowledge of the actual liquid aspiration can be more accurately determined.

The following is a copy of a coded source routine in C++ adapted to obtain multiple air aspirations and obtain a representative pressure reference value according to the methods described herein.

```
Collect baseline data while aspirating air
void emeProbeBase::CollectAirBaselineData(int a_nCollectMeterPumpBaselines)
{
    if(ShortAspirationDetectionEnabled( )&& a_nCollectMeterPumpBaselines > 0)
    {
        FileLog( )->FileLog(_T(" Air baseline\n"));
        // Raise probe out of drain
        GetArm( )->Raise( );
        if(ValidSetupValue(enProbeOverTypeCFlexWell5))
        {
            // Move probe over flex
            MoveArm(enProbeOverTypeCFlexWell5, enArmIndexFlex, true);
            // Lower probe to offset 2mm above top of flex
            MoveVertical(enFormDefaultCmd, enProbeTopOfFlex, 2.0, true);
            for (int n=0; n < a_nCollectMeterPumpBaselines; n++)
            {
                FileLog( )->FileLog(_T(" Meter pump baseline (%d of %d)\n"),
                            n+1, a_nCollectMeterPumpBaselines);
                SleepRelative(1000);
                // Aspirate with meter pump, collect and process clog data
                GetProbe( )->CollectMeterPumpBaselineData( );
            }
            // Save statistics core dump file after updating baselines
            PersistStatistics( );
            // Raise probe out of flex slot
            Get Arm( )->Raise( );
            // Move the probe back over the drain
            MoveArm(enProbeOverDrain, enArmIndexDrain, true);
        }
        // Put probe back down into drain
        MoveVertical(enFormDefaultCmd, enProbeHeightInDrain, 0.0, true);
    }
}
// CollectMeterPumpBaselineData( )
bool devProbeSyringe::CollectMeterPumpBaselineData(int a_nIndex)
{
    bool l_bSuccess = false;
    try
    {
        if (a_nIndex >= 0 && a_nIndex < m_nNumMeterPumpSpeeds)
        {
            if (MeterPumpSpeeds[a_nIndex].Volume > 0)
            {
                FormCommandIdEnum l_enFormCmdId = MeterPumpSpeeds[a_nIndex].CmdId;
                double l_dVolume = MeterPumpSpeeds[a_nIndex].Volume;
                int l_nSpeedLimit = MeterPumpSpeeds[a_nIndex].Limit;
                double l_dPressureReading[NUM_BASELINE_READS];
                // Aspirate an air gap
                Aspirate(enFormDefaultCmd, 10, true, true);
```

```
            SleepRelative(250);
            for (int n = 0; n < NUM_BASELINE_READS; n++)
            {
                SleepRelative(50);
                // Aspirate using meter pump w/o waiting
                Aspirate(l_enFormCmdId, l_dVolume, true, false);
                // Collect and process transducer data
                CollectMeterPumpData(enClogDetectMeterPumpBaseline);
                // Add the new pressure reading value to the array
                l_dPressureReading[n] = m_ClogDetector.MeterPumpBaseline( );
                // Dispense to move the piston back where we started
                Dispense(enFormDefaultCmd, l_dVolume, true);
            }
            // Dispense all to move the piston back to home
            Dispense All(enFormDefaultCmd, true);
            // Sort the baseline readings so we can find the median
            libStatistics::ShellSort(l_dPressureReading, NUM_BASELINE_READS);
            // The new baseline is the median of the five readings
            double l_dNewBaseline = l_dPressureReading[NUM_BASELINE_READS/2];
            // Get a pointer to the persisted statistics object
            ProbeStatisticsEnum l_enStatistics =
                        MapPumpSpeedToStatisticsObj(MeterPumpSpeeds[a_nIndex].CmdId);
            esmStatisticsObj *l_pStatisticsObj = GetProbe( )->GetStatisticsObj(l_enStatistics);
            int l_nErrorCode = MAP_ERR_NONE;
            // Have we previously saved enough values to trust the statistics?
            // Skip the check if no speed limit is set.
            if (l_pStatisticsObj != NULL && l_nSpeedLimit > 0 &&
                    l_pStatisticsObj->NumValues( ) >= MIN_METER_PUMP_BASELINES)
            {
                // Compare new baseline value to statistical values
                double l_dLimit = min(l_nSpeedLimit/2, max(75, 3*l_pStatisticsObj->StdDev( )));
                double l_dDelta = abs(l_dNewBaseline - l_pStatisticsObj->Mean( ));
                if (l_dDelta > l_dLimit || m_ClogDetector.ClearInjectedClogError( ))
                {
                    if (GetProbe( )->IncrementShortAspirationErrorCount( ) == 1)
                    {
                        l_nErrorCode = MAP_ERR_CLOG_DETECTOR_METER_PUMP_BASELINE_FAILED;
                    }
                    else
                    {
                        l_nErrorCode                                                    =
MAP_ERR_CLOG_DETECTOR_METER_PUMP_BASELINE_PERSISTENT_ERROR;
                        GetProbe( )->DisableShortAspirationDetection( );
                    }
                    cdvCriticalError(_T("CollectMeterPumpBaselineData( )"),
                            _T("Meter Pump bad baseline: %.1f > %.1f - baseline=%.1f mean=%.1f sd=%.1f
errors=%d"),
                            l_dDelta, l_dLimit, l_dNewBaseline, l_pStatisticsObj->Mean( ),
                            l_pStatisticsObj->StdDev( ), GetProbe( )->ShortAspirationErrorCount( ));
                }
                else
                {
                    GetProbe( )->ClearShortAspirationErrorCount( );
                }
            }
            if (l_nErrorCode == MAP_ERR_NONE)
            {
                // Start using the new baseline
                MeterPumpSpeeds[a_nIndex].Baseline = l_dNewBaseline;
            }
            // Calculate absolute error limit by subtracting delta limit from baseline
            double      l_dErrorLimit     =     MeterPumpSpeeds[a_nIndex].Baseline     -
MeterPumpSpeeds[a_nIndex].Limit;
            // SCMS 38039 (3.5) - Set error limit as property instead of baseline
            if (MeterPumpSpeeds[a_nIndex].enPropertyId > PROP_UNINITIALIZED_PROPERTY)
                InstrumentStatus( )->SetPropertyValue(MeterPumpSpeeds[a_nIndex].enPropertyId,
l_dErrorLimit);
            if (l_pStatisticsObj != NULL)
            {
                // Don't save the new baseline value to the statistics object if there was an error
                if (l_nErrorCode == MAP_ERR_NONE)
                    l_pStatisticsObj->NewValue(l_dNewBaseline);
                cdvTrace(_T(" CollectMeterPumpBaselineData"),
                        _T("cmd=%s baseline=%.1f limit=%.1f mean=%.1f sdev=%.1f cv=%.1f%% num=%d"),
                        FormCommandId::ToString(MeterPumpSpeeds[a_nIndex].CmdId), l_dNewBaseline,
```

-continued

```
                    l_dErrorLimit, l_pStatisticsObj->Mean( ), l_pStatisticsObj->StdDev( ),
                    l_pStatisticsObj->PercentCV( ), l_pStatisticsObj->NumUpdates( ));
            LPCTSTR l_pErrorString = l_nErrorCode == MAP_ERR_NONE ? _T("") :
InstrErrorCode::ToString(l_nErrorCode);
                PostStatisticsEvent(l_pStatisticsObj,
                                enServiceEventMeterPumpBaseline,
                                enServiceParamNamePumpSpeed,
                                FormCommandId::ToString(MeterPumpSpeeds[a_nIndex].CmdId),
                                l_dNewBaseline, l_dErrorLimit, l_pErrorString);
            }
            else
            {
                cdvTrace(_T("CollectMeterPumpBaselineData"), _T("cmd=%s baseline=%.1f limit=%.1f"),
                                FormCommandId::ToString(l_enFormCmdId), l_dNewBaseline, l_dErrorLimit);
            }
            if (l_nErrorCode != MAP_ERR_NONE)
            {
                throw libErrorObj(l_nErrorCode, GetTypeId( ),
                                _T("%s: ProcessDataErrors( ): Meter pump bad baseline\n"),
                                GetTypeName( ));
            }
            l_bSuccess = true;
        }
    }
    }
    catch( libErrorObj &TheError )
    {
        TheError.AddErrorContext(_T("%s: %s"), GetTypeName( ),
                        _T("CollectMeterPumpBaselineData\n"));
        throw;
    }
    return l_bSuccess;
}
```

While the invention is susceptible to various modifications and alternative forms, specific system embodiments and methods thereof have been shown by way of example in the drawings and are described in detail herein. It should be understood, however, that it is not intended to limit the invention to the particular systems or methods disclosed but, to the contrary, the intention is to cover all modifications, equivalents, and alternatives falling within the scope of the invention. In memory of Michael Kaplit.

What is claimed is:

1. A method of calibrating a liquid transfer system, comprising:
    providing a probe having a pressure sensor fluidly coupled to the probe;
    performing multiple air aspirations by aspirating air across a known or expected liquid aspiration volume or flow rate range to be used in the liquid transfer system and then expelling the air for each of the multiple aspirations, and taking multiple representative pressure readings with the pressure sensor of only the multiple air aspirations; and
    using the multiple representative pressure readings to calibrate the pressure sensor to verify that an appropriate amount of liquid is aspirated during liquid aspirations.

2. The method of claim 1, further comprising:
    moving the probe to a defined location in space prior to performing the multiple air aspirations.

3. The method of claim 2, wherein the defined location in space is over a liquid-containing vessel.

4. The method of claim 3, wherein the liquid-containing vessel comprises a reagent container.

5. The method of claim 3, wherein the defined location in space is located less than 20 mm from the liquid-containing vessel.

6. The method of claim 1, further comprising:
    recording at least some of the multiple representative pressure readings for at least some of the multiple air aspirations; and
    determining a representative pressure reference value for the multiple representative pressure readings.

7. The method of claim 6, wherein the representative pressure reference value is a median value of the multiple representative pressure readings.

8. The method of claim 6, wherein the multiple air aspirations comprise three or more air aspirations.

9. The method of claim 6, wherein the multiple air aspirations comprise five or more air aspirations.

10. The method of claim 6, wherein at least two of the multiple air aspirations are carried out by aspirating different air volumes.

11. The method of claim 6, wherein at least two of the multiple air aspirations are carried out by aspirating at different aspiration flow rates.

12. The method of claim 6, wherein the at least two of the multiple air aspirations are carried out by aspirating at different air volumes and at different aspiration flow rates.

13. The method of claim 1, wherein the multiple air aspirations comprise:
    a first set of air aspirations at a first aspiration flow rate and a first aspiration volume; and
    a second set of air aspirations at a second aspiration flow rate and a second aspiration volume, the second aspiration flow rate being different from the first aspiration flow rate, and the second aspiration volume being different from the first aspiration volume.

14. The method of claim 1, comprising:
    providing multiple probes in the liquid transfer system, and
    carrying out separate air aspirations for each probe in the liquid transfer system.

15. The method of claim 1, comprising:
aspirating a volume of a specimen or a reagent liquid; and
using a representative pressure reference value obtained from the calibration of the pressure sensor to determine if a sufficient volume of the specimen or the reagent liquid has been aspirated.

16. The method of claim 1, comprising generating a representative pressure reference value based upon multiple air aspirations.

17. A method of calibrating a liquid transfer system, comprising:
providing a probe having a pressure sensor fluidly coupled to the probe, the pressure sensor adapted to sense a representative aspiration pressure;
moving the probe to a defined location in space above a liquid-containing vessel;
performing multiple air aspirations across a known or expected liquid aspiration volume or flow rate range to be used in the liquid transfer system at the defined location wherein at least some of the multiple air aspirations are at a different aspiration flow rate and at least some of the multiple air aspirations are at a different aspiration volume;
recording pressure readings of at least some of the multiple air aspirations; and
using at least some of only the recorded pressure readings to determine a representative pressure reference value to calibrate the pressure sensor to verify that an appropriate amount of liquid is aspirated during liquid aspirations.

18. A liquid transfer system, comprising:
a probe;
a pressure sensor fluidly coupled to the probe, the pressure sensor adapted to sense a representative aspiration pressure; and
a controller configured and operational to perform multiple air aspirations by aspirating air across a known or expected liquid aspiration volume or flow rate range to be used in the liquid transfer system and then expelling the air for each of the multiple aspirations, to record multiple pressure readings based upon the multiple air aspirations, and to determine a representative pressure reference value to calibrate the pressure sensor to verify that an appropriate amount of liquid is aspirated during liquid aspirations based on only the multiple pressure readings.

* * * * *